United States Patent [19]

Kim

[11] Patent Number: 4,569,843

[45] Date of Patent: Feb. 11, 1986

[54] METHOD OF TREATMENT DURING WITHDRAWAL FROM DRUG DEPENDENCY

[76] Inventor: Tuk M. Kim, 2546 San Bruno Ave., San Francisco, Calif. 94134

[21] Appl. No.: 586,060

[22] Filed: Mar. 5, 1984

[51] Int. Cl.$^4$ ............................................. A61K 35/78
[52] U.S. Cl. .................................................... 424/195.1
[58] Field of Search .............................. 424/195, 195.1

[56] References Cited

U.S. PATENT DOCUMENTS 4,409,144 10/1983 Heinicke ........................ 260/236.5

OTHER PUBLICATIONS

Chinese Herbs Dictionary, edited in Shanghai 1977, pp. 876–879, 2710–2712, 1672–1673 and 1727–1728.

*Primary Examiner*—Albert T. Meyers
*Assistant Examiner*—John W. Rollins, Jr.
*Attorney, Agent, or Firm*—Flehr, Hohbach, Test, Albritton & Herbert

[57] ABSTRACT

A method is provided for treatment of drug dependent subjects comprising the step of orally administering to such subjects during the period of drug withdrawal an herbal composition comprising *Radix angelica sinensis, Herba pogostemi, Cyperus rotundus* and *Squama manitis pendactilae.*

6 Claims, No Drawings

METHOD OF TREATMENT DURING WITHDRAWAL FROM DRUG DEPENDENCY

The present invention is directed to a method for treating persons during withdrawal from drug dependency. In particular, the present invention is directed to method of treatment during withdrawal from drug dependency comprising orally administering an herbal composition.

During the period of withdrawal from drug dependency, particularly in the case of addictive narcotics, a drug dependent subject will normally experience withdrawal symptoms. The symptoms normally include physical manifestations due to the body's elimination process of the toxic narcotic products accumulated in the blood, internal passages, and organs. The physical withdrawal symptoms may include tearing, discharges of bronchial mucous, excessive perspiration, diarrhea, vomiting, dark urine and spasmodic attacks. Other withdrawal symptoms result from the effect of the addictive drug on the nervous system which is usually depressed and weakened from the prolonged use of the drug. These symptoms include irritability, anxiety, depression, headaches and various pains throughout the body. These withdrawal symptoms are not an indication of disease but rather an indication that the body is restoring itself to a healthy state. The symptoms are therefore a part of the natural effect of the self-healing capabilities of the body through the elimination of toxic waste products.

It is, therefore, an object of the present invention to provide a method of treatment of persons undergoing drug dependency withdrawal to alleviate, and in some cases, eliminate the unpleasantness accompanying the withdrawal.

It is a further object of the invention to assist natural processes of detoxification and elimination of toxic products from the blood and body, and provide fresh new elements required by the body.

According to the present invention a method is provided for alleviating the unpleasantness of withdrawal by administering to the subject periodic unit doses of an herbal composition comprising the following four components: *Radix angelica sinensis, Herba pogostemi, Cyperus rotundus* and *Squama manitis pendactilae*. The herb *Pogostemon cablin* may be alternatively used in place of the *Herba pogostemi*. The first three of these herbs are commercially available and are indigenous to Asia. The last herb is also commercially available and is an epidermal scale from wild animals. Preferably, the herbs will be formulated into unit dosage forms so that the unit doses may be administered periodically during the period of drug withdrawal. While the relative proportions of the herbs in each unit dose is not critical, it is preferred that each of the *Radix angelica sinensis, Herba pogostemi* and *Cyperus rotundus* be utilized in approximately equal proportions and that the amount of *Squama manitis pendactilae* be utilized in a greater proportion than any other single herbal ingredient. Preferably, 1 to 5 parts by weight each of the *Radix angelica sinensis, Herba pogostemi* and *Cyperus rotundus* may be utilized with 2 to 10 parts by weight of the *Squama manitis pendactilae*. Most preferred is a proportion of *Radix angelica sinensis: Herba pogostemi: Cyperus rotundus: Squama manitis pendactilae* of 1:1:1:3.

Preferably, each ingredient should be separately triturated, as for example, by mortar and pestle, until they are reduced to a fine powder. In its natural state, *Cyperus rotundus* is characterized by a fuzzy exterior and this fuzz should be eliminated first by roasting then by trituration whereby the fuzz will be easily pulverized. Before trituration, the *Squama manitis pendactilae* must be roasted with sand to a golden color.

The composition is to be administered orally and preferably should be prepared in unit dosage forms. A unit dosage will comprise from 1 to about 5 grams per dose, preferably, about 3 grams per dose. The composition may be administered in the form of a powder, capsule, solution, tablet, and the like. The composition may be formed into conventional tablets and capsules utilizing pharmaceutically acceptable inert carriers such as lactose, glucose, gelatin, and the like. Preferably, the composition may be mixed with lactose or other sweetening agent since the sweet taste is soothing to the stomach.

The frequency of treatment will depend upon the individual subject, the degree of drug dependency, body weight and the general state of health. Typically, for the first four days of drug withdrawal, about 10 dosage units (3 grams per unit dose) may be administered per day, at intervals of about 2 to 2½ hours. During the next four days, approximately six doses may be administered per day at intervals of 4 hours. After this, three doses per day may be administered, one dose every 8 hours for several days according to the condition of the subject.

It has surprisingly been found that during the period of withdrawal when utilizing the composition according to the present invention, the withdrawal pain is substantially decreased at a rapid rate and, furthermore, the compositions according to the present invention appear to cause a violent physical reaction in the subject if an opiate such as morphine is taken during the withdrawal period. For example, when being treated with the composition according to the present invention, an injection of morphine may cause a patient to become sick with fever and pain, thereby greatly reducing the tendency of the subject to return to drug dependency.

The herbs according to the present invention have the following characteristics. *Radix angelica sinensis* is spicy sweet with a warm and bitter aftertaste. According to traditional herbal pharmacology this herb is believed to vitalize and balance the blood by eliminating toxic elements, assist in the metabolism and secretion of hormones, and to have a slight tranquilizing and pain relieving effect. *Herba pogostemi* is spicy to taste with a warm aftertaste and is believed to promote elimination of waste products being helpful in relieving vomiting, diarrhea and relieving headaches and abdominal pain. *Cyperus rotundus* is spicy, bitter-sweet and neutral and is believed to assist in blood circulation and suppressing headache and stomach cramps. *Squama manitis pendactilae* is salty and slightly toxic unless heated to a golden color before use. It is believed to assist in excretion and secretion, as well as relieving pain and soothing the nervous system.

Having described the specific embodiments of the present invention, the following are examples. However, the following examples are intended to be illustrative of the invention and the invention is not intended to be limited thereby.

EXAMPLE 1

A thirty-two year old male addicted to heroin was treated according to the present invention using a unit dosage form of 3 grams containing *Radix angelica sinensis, Herba pogostemi, Cyperus rotundus* and *Squama manitis pendactilae* in proportions of 1:1:1:3. The subject was treated for four days using 10 doses per day orally administered every 2½ hours; then four days using 6 doses administered every 4 hours, then four days using 3 doses administered every 8 hours. The subject experienced no serious pain and subsequent to the treatment confirmed that heroin use had discontinued. The subject had previously had been an heroin addict for about six months.

EXAMPLE 2

A twenty-nine year old female addicted to heroin was treated for twelve days according to the treatment described above in Example 1. The subject previously had a 6-month addiction to heroin. During treatment, the subject experienced no serious pain and subsequent to treatment confirmed that heroin use had ceased.

EXAMPLE 3

A 35 year old male having an addiction to heroin was treated for two weeks with the herbal composition described in Example 1. The addiction was cured without any serious withdrawal pain.

EXAMPLE 4

The subject is a 33 year old female, mother of 2 children, complaining of runny nose, backache, irritation, and lack of energy, with a history of occasional heroin use for the past nine years, with increasing recent heroin use. She was treated for 12 days with the herbal composition described in Example 1. After treatment she was cured of the addiction.

EXAMPLE 5

A 43 year old male having a four month old habit of heroin addiction was treated for 10 days with the herbal composition described in Example 1. He was cured of the addiction after treatment.

EXAMPLE 6

A 37 year old female having a four month old habit of heroin addiction was treated as in Example 5. After 10 days of treatment, the subject was cured of the addiction.

What is claimed is:

1. A method for treatment of heroin dependent subjects comprising the step of orally administering during the period of drug withdrawal a composition comprising powdered *Radix angelica sinensis, Herba pogostemi, Cyperus rotundus* and *Squama manitis pendactilae* in unit dosage form.

2. A method according to claim 1 wherein said unit dosage comprises the components in proportion of 1–5 parts each of *Radix angelica sinensis, Herba pogostemi, Cyperus rotundus* and 2–10 parts of *Squama manitis pendactilae*.

3. A method according to claim 2 wherein said unit dosage comprises a total of 1 to 5 grams.

4. A method according to claim 3 wherein said unit dosage comprises 3 grams.

5. A method according to claim 4 wherein said unit dosage is administered in intervals from 2 to 8 hours per day.

6. A method according to claim 3 wherein said properties are 1 part each of *Radix angelica sinensis, Herba pogostemi* and *Cyperus rotundus* and 3 parts of *Squama manitis pendactilae*.

* * * * *